(12) United States Patent
Walther et al.

(10) Patent No.: US 6,660,833 B1
(45) Date of Patent: Dec. 9, 2003

(54) RESPIRATORY DISTRESS SYNDROME THERAPY WITH PEPTIDE ANALOGS OF HUMAN SP-B

(75) Inventors: Frans J. Walther, Hermosa Beach, CA (US); Alan J. Waring, Irvine, CA (US); Larry M. Gordon, Del Mar, CA (US); Joseph A. Zasadzinski, Santa Barbara, CA (US)

(73) Assignee: Harbor-UCLA Research and Education Institute, Torrance, CA (US)

(*) Notice: Subject to any disclaimer, the term of this patent is extended or adjusted under 35 U.S.C. 154(b) by 0 days.

(21) Appl. No.: 09/515,356

(22) Filed: Feb. 29, 2000

(51) Int. Cl.$^7$ .......................... A61K 38/00; A61K 38/16

(52) U.S. Cl. ............................. 530/324; 514/8; 514/12

(58) Field of Search .............................. 530/324; 514/8, 514/12

(56) References Cited

U.S. PATENT DOCUMENTS

| | | |
|---|---|---|
| 5,547,937 A | 8/1996 | Dhaon et al. |
| 5,861,481 A | 1/1999 | McLean et al. |
| 5,874,406 A | 2/1999 | Schafer et al. |
| 5,876,970 A | 3/1999 | Benson et al. |

OTHER PUBLICATIONS

Sarin, V.K. et al., "Biophysical and Biological Activity of a Synthetic 8.7–kDa Hydrophobic Pulmonary Surfactant Protein SP–B." Proc. Natl. Acad. Sci. USA 87:2633–2637, 1990.

Cochrane, C.G. and S.D. Revak. "Pulmonary Surfactant Protein B (SP–B): Structure–Bunction Relationships." Science 254:566–568, 1991.

Johansson, J. et al., " Human Surfactant Polypeptide SP–B: Disulfide bridges, C–terminal end, and peptide analysis of the airway form." FEBS Lett. 301: 165–167, 1992.

Pilot–Matias, T.J. et al., "Structure and Organization of the Gene Encoding Human Pulmonary Surfactant Proteoplipid SP–B." DNA 8: 75–86, 1989.

Fan, B.R. et al., "Antibodies against Synthetic Amphipathic Helical Sequences of Surfactant Protein SP–B Detect a Conformational Change in the Native Protein." FEBS Lett. 282:220–224, 1991.

Longo, M.L. et al., "A Function of Lung Surfactant Protein SP–B." Science 261: 453–456, 1993.

Bruni, R. et al., "Surfactant Protein B: Lipid Interactions of Synthetic Peptides Representing the Amino–Terminal Amphipathic Domain." Proc. Natl. Acad. Sci. USA 88:7451–7455, 1991.

Gordon, L.M. et al., "Conformation and Molecular Topography of the N–terminal Segment of Surfactant Protein B in Structure–Promoting Environments." Protein Science 5: 1662–1675, 1996.

Walther, F.J. et al., "Spiking Survanta with Synthetic Surfactant Peptides Improves Oxygenation in Surfactant–deficient Rats." Am. J. Respir. Crit. Care Med. 156: 855–861, 1997.

Walther, F.J. et al., "Protein Composition of synthetic Surfactant Affects Gas Exchange in Surfactant–Deficient Rats." Pediatric Research 43: 666–673 1998.

Mbagwu, N. et al., "Sensitivity of Synthetic Surfactants to Albumin Inhibition in Preterm Rabbits." Mol. Gen. Metabol. 66: 40–48, 1999.

Gupta, M. et al., "Function and Inhibition Sensitivity in Preter Rabbits of Surfactant with Various Surfactant Protein B Sequences." submitted for publication Oct. 5, 1999.

Lipp, M.M. et al., "Solving Medical Problems with Chemical Engineering." Chemtech, Mar. , 1997 p. 42–47.

Lipp, M.M. et al. "Phase and Morphology Changes in Lipid Monolayers Induced by SP–B Protein and its Amino–Terminal Peptide." Science 273: 1196–1199.

Waring, A.J., et al. "Amphipathic Helical Segments in Lung Surfactant Proteins." in *The Amphipathic Helix*, ed. R.M. Epand, CRC Press, Boca Raton, 143–171, 1993.

Waring, A., et al. "Synthetic Amphipathic Sequences of Surfactant Protein–B Mimic Several Physicochemical and In Vivo Properties of Native Pulmonary Surfactant Proteins." Peptide Research 2: 308–313, 1989.

Amirkhanian, J.D. et al. "Inhibition of Mixtures of Surfactant Lipids and Synthetic Sequences of Surfactant Proteins SP–B and SP–C." Biochem. Biophys. Acta 1096: 355–360, 1991.

Lipp, M.M. et al., "Phase and Morphology Changes in Lipid Monolayers Induced by SP–B Protein and Its Amino–Terminal Peptide." Science 273: 1196–1199.

Yong, H. et al., Expression of an Engineered Cecropin Gene Cassette in Transgenic Tobacco Plants Confers Disease Reseistance to *Pseudomonas Syringae PV Tabaci*. Agricultural Research Service: May 22, 1996.

Veldhuizen, J.A., et al., "A Dimeric Version of the SP–B 1–25 Peptide has an Increased Surface Activity In Vitro." Abstract submitted to American Thoracic Society for presentation, May 2000.

(List continued on next page.)

Primary Examiner—Christopher S. F. Low
Assistant Examiner—Rita Mitra
(74) Attorney, Agent, or Firm—Orrick, Herrington & Sutcliffe LLP; Kurt T. Mulville (57) ABSTRACT

A therapeutic pharmaceutical composition for the treatment of respiratory disease is disclosed, including particularly Respiratory Distress Syndrome (RDS). The composition is comprised of a synthetic dimer of an N-terminal fragment of Surfactant Protein B (SP-B) that advantageously mimics the functional activity of native human Surfactant Protein B, and to therapeutic methods of administration of such pharmaceutical compositions.

8 Claims, 7 Drawing Sheets

OTHER PUBLICATIONS

Gupta, M. et al., "Dimeric versus Monomeric SP–B 1–25 Peptide and Lung Function in Preterm Rabbits." Abstract submitted to American Thoracic Society for presentation, May 2000.

Walther, F.J. et al., "The Effect of synthetic Surfactants with Dimeric and Monomeric SP–B1–25 Peptide on Lung Function in Lavaged Rats." Abstract submitted to American Thoracic Society for presentation, May 2000.

Lee, K.Y.C. et al., "A Synchrotron X–ray Study of Lung Surfactant Specific Protein SP–B into Lipid Monolayers at the Air–Fluid Interface." submitted for publication Jun. 19, 1999.

Gordon, L.M. et al., "Conformational Mapping of the N–terminal Segment of Surfactant Protein B in Lipid Using $^{13}$C–enhanced Fourier Transform Infrared Spectroscopy." submitted for publication Jul. 23, 1999.

Lipp, M.M. et al., "Coexistence of Buckled and Flat Monolayers." Physical Rev. Letters 81: 1650–1653, 1998.

Longo, M.L. et al., "Lipid Bilayer surface Association of Lung Surfactant Protein SP–B, Amphipathic Segment Detected by Flow Immunofluorescence." Biophys. J. 63; 760–773.

daCosta, D.E. et al., "Comparative Trial of Artificial and Natural Surfactants in the Treatment of Respiratory Distress Syndrome of Prematurity: Experiences in a Developing Country." Pediatr. Pulmonol. 27: 312–317, 1999.

NH₂ Phe Pro Ile Pro Leu Pro Tyr Cys Trp Leu Cys Arg Ala Leu Ile
Lys Arg Ile Gln Ala Met Ile Pro Lys Gly Ala Leu Ala Val Ala Val
Ala Gln Val Cys Arg Val Val Pro Leu Val Ala Gly Gly Ile Cys
Gln Cys Leu Ala Glu Arg Tyr Ser Val Ile Leu Leu Asp Thr Leu
Leu Gly Arg Met Leu Pro Gln Leu Val Cys Arg Leu Val Leu Arg
Cys Ser Met-COOH

*FIG. 1*

Native Human SP-B 1-25

NH₂-F P I P L P Y C W L C R A L I K R I Q A M I P K G - COOH

SP-B 1-25 (Cys-11 > Ala-11) variant monomer

NH₂-F P I P L P Y C W L A R A L I K R I Q A M I P K G - COOH

Amino acid sequence of SP-B 1-25 (Cys-11 > Ala-11) variant monomer

*FIG. 2*

SP-B 1-25 (Cys-11 > Ala-11) variant disulfide linked homodimer

NH₂-F P I P L P Y C W L A R A L I K R I Q A M I P K G - COOH
                    |
                    S
                    |
                    S
                    |
NH₂-F P I P L P Y C W L A R A L I K R I Q A M I P K G - COOH

Amino acid sequence of SP-B 1-25 (Cys-11 > Ala-11) variant homodimer

Electrospray SP-B 1-25 (Cys-11 > Ala-11) variant disulfide linked homodimer

SEQUENCE LISTING

<160> NUMBER OF SEQ ID NOS: 4

<210> SEQ ID NO 1
<211> LENGTH: 79
<212> TYPE: PRT
<213> ORGANISM: Homo sapiens

<400> SEQUENCE: 1

```
Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu Arg Tyr Ser Val Ile Leu Leu Asp Thr Leu Leu Gly Arg
    50                  55                  60

Met Leu Pro Gln Leu Val Cys Arg Leu Val Leu Arg Cys Ser Met
65                  70                  75
```

<210> SEQ ID NO 2
<211> LENGTH: 25
<212> TYPE: PRT
<213> ORGANISM: Homo sapiens
<220> FEATURE:
<221> NAME/KEY: misc_feature
<223> OTHER INFORMATION: Native Human SP-B 1-25

<400> SEQUENCE: 2

```
Phe Pro Ile Pro Leu Pro Tyr Cys Trp Leu Cys Arg Ala Leu Ile Lys
1               5                   10                  15

Arg Ile Gln Ala Met Ile Pro Lys Gly
            20                  25
```

<210> SEQ ID NO 3
<211> LENGTH: 25
<212> TYPE: PRT
<213> ORGANISM: Homo sapiens
<220> FEATURE:
<221> NAME/KEY: misc_feature
<222> LOCATION: (11)..(11)
<223> OTHER INFORMATION: SP-B 1-25 (Cys-11 > Ala-11) variant monomer

<400> SEQUENCE: 3

```
Phe Pro Ile Pro Leu Pro Tyr Cys Trp Leu Ala Arg Ala Leu Ile Lys
1               5                   10                  15

Arg Ile Gln Ala Met Ile Pro Lys Gly
            20                  25
```

<210> SEQ ID NO 4
<211> LENGTH: 25
<212> TYPE: PRT
<213> ORGANISM: Homo sapiens
<220> FEATURE:
<221> NAME/KEY: misc_feature
<222> LOCATION: (11)..(11)
<223> OTHER INFORMATION: SP-B 1-25 (Cys-11 > Ala-11) variant
<221> NAME/KEY: misc_feature
<222> LOCATION: (8)..(8)
<223> OTHER INFORMATION: Peptide crosslinked through cysteine sulfhydryl
     to form homodimer

```
-continued

<400> SEQUENCE: 4

Phe Pro Ile Pro Leu Pro Tyr Cys Trp Leu Ala Arg Ala Leu Ile Lys
1               5                   10                  15

Arg Ile Gln Ala Met Ile Pro Lys Gly
                20                  25
```

RESPIRATORY DISTRESS SYNDROME THERAPY WITH PEPTIDE ANALOGS OF HUMAN SP-B

This invention was made in part from government support under Grant Nos. RO1 HL 55543 and RO1 HL 51177 from the National Institute of Health (NIH) of the United States. The U.S. Government may have certain rights in this invention.

FIELD OF THE INVENTION

The present invention relates generally to a therapeutic pharmaceutical composition for the treatment of respiratory disease, including particularly Respiratory Distress Syndrome (RDS) comprised of a synthetic dimer of an N-terminal fragment of Surfactant Protein B (SP-B) that advantageously mimics the functional activity of native human Surfactant Protein B, and to therapeutic methods of administration of such pharmaceutical compositions.

BACKGROUND

The human lung is composed of a large number of small air sacs, called alveoli, in which gases are exchanged between the blood and the air spaces of the lungs. In healthy individuals, this exchange is mediated by the presence of a protein-containing surfactant complex. Lung surfactant complex is composed primarily of lipid and contains a minor component of various proteins. An absence of adequate levels of this complex results in malfunction of the lung. This syndrome is called Respiratory Distress Syndrome (RDS). Adult RDS is correlated with an absence or dysfunction of the lung surfactant at the alveoli membrane where the gas exchange occurs. The adult disease results from lung insults such as diffuse infections, aspiration of the gastric contents or water, inhalation of irritants and toxins and pulmonary edema arising from such sources as narcotic overdose. The syndrome is also common in premature infants and is associated with immaturity and low birth weight. Of those pre-term infants afflicted, approximately 10% die. Infantile respiratory distress syndrome is the leading cause of death in the first twenty-eight days of life.

Patients with RDS exhibit either abnormal quantities of lung surfactant, an abnormal composition of lung surfactant, or both. Successful treatments focus on replacing surfactant levels and composition to the normal range through surfactant replacement therapy. At the alveolar level, lung surfactant functions prevent excessive accumulation of liquid within the alveolar airspace and stabilize the alveoli and small airways against collapse. A lung surfactant deficiency results in the collapse of the alveoli causing respiratory distress. Surfactant replacement therapy can be used either prophylactically or as rescue treatment for patients with clinical signs of RDS.

The composition of native lung surfactant is lipid (approximately 90%–97%) and various proteins (approximately 10%). The primary lipid type is phospholipid and constitutes 97% of the total lipid. 80% of this phospholipid is phosphatidylcholine (PC) and 10% is phosphatidyglycerol (PG). 70–80% of the phospholipid acyl chains are saturated. The major lipid is dipalmitoylphosphatidylcholine (DPPC). Four surfactant-associated proteins are known to exist: two are glycoproteins, SP-A and SP-D, and two are small hydrophobic proteins, SP-C and SP-B.

Human lung surfactant contains a hydrophobic SP-B peptide, which is usually present as a dimer. The SP-B functions by reducing the surface tension of alveoli to prevent collapse of the lung air sacs, thereby preventing respiratory distress. In the past, surfactant replacement therapies focused on using the lipid components alone. It was later found that the therapy's performance was greatly improved by the use of the apoprotein in similar proportion to native human surfactant.

Current RDS therapies generally attempt to either utilize natural SP-B or SP-C from other mammals or to synthesize a protein with the functional equivalent of human SP-B. Of the commercially available treatments, the majority utilize natural or modified-natural lung surfactants instead of synthetic surfactants. The natural, animal derived, lung surfactants are harvested from animal lungs either by organic solvent extracts of lung lavage or by organic solvent extracts of minced lungs. The following are commercially available lung surfactants: Curosurf, manufactured by Cheisi Farmeceutici of Italy, is such a natural lung surfactant derived from porcine lung lavage extract. Curosurf contains DPPC in similar proportion to human surfactant and SP-B & SP-C. Another natural lung surfactant, Infasurf, manufactured by Forest Laboratories, is a natural surfactant extract from calf lung lavage. Infasurf is also comprised of phospholipids and SP-B & SP-C. Another commercially available natural lung surfactant is Survanta®, manufactured by Abbott Labs, a chemically modified natural bovine lung extract. The only synthetic lung surfactant therapy commercially available, Exosurf, manufactured by Glaxo Wellcome, is a synthetic protein free surfactant composed of eighty-five percent DPPC, nine- percent hexadecanol and six-percent tyloxapol. Surfactant replacement therapy can be used either prophylactically or as a rescue treatment for patients with clinical signs of RDS.

SUMMARY OF THE INVENTION

The present invention includes a pharmaceutical composition of synthetic peptides used to treat respiratory disorders. The composition may also be added to existing treatments to enhance the biological activity of existing pulmonary surfactant dispersions for the treatment of RDS. The invention preferably provides a composition of novel synthetic peptide analogs of SP-B that mimic the active site of native Surfactant Protein B (SP-B) SEQ ID NO: 1. The composition of the invention may be used to supplement naturally derived lung surfactants or to formulate synthetic lung surfactant lipid-peptide dispersions. See Walther, F. J., Hernandez- Juviel, J., Bruni, R., Waring, A. J., "Spiking Survanta with Synthetic Surfactant Peptides Improves Oxygenation in Surfactant-deficient Rats," Am. J. Respir. Crit. Care Med., Vol. 156:855–861, 1997. Unlike protein free formulations, the synthetic peptide of the present invention mimics the active site of the SP-B protein and creates a synthetic analog of these amino acids to augment the properties of the native proteins.

The SP-B analogs of the present invention are based on the known primary sequence of native mammalian SP-B and in a preferred embodiment, human SP-B (SEQ ID NO:2). Specifically, in one preferred embodiment, a covalently linked dimer of the constituent N-terminus SP-B domain (amino acids 1–25), herein referred to as the SP-B1–25 dimer (SEQ ID NO:2), may replace or supplement full length proteins currently used to treat RDS. Because the human peptide is more effective than other natural SP-B derived from animal sources, the creation of a synthetic peptide that mimics human SP-B is more efficacious in the treatment of RDS than natural surfactants derived from animals. Furthermore, the dimeric SP-B1–25 e (SEQ ID NO:2) exhibits advantageous physical and chemical characteristics in analyses that reflect the desired properties of surface tension at the air/liquid interface of the lung. The SP-B1–25 dimer can be formulated in therapeutic compositions for the treatment of respiratory disorders, and can be used in methods designed to treat respiratory disorders when clinically indicated.

DETAILED DESCRIPTION OF THE INVENTION

Figure 3:
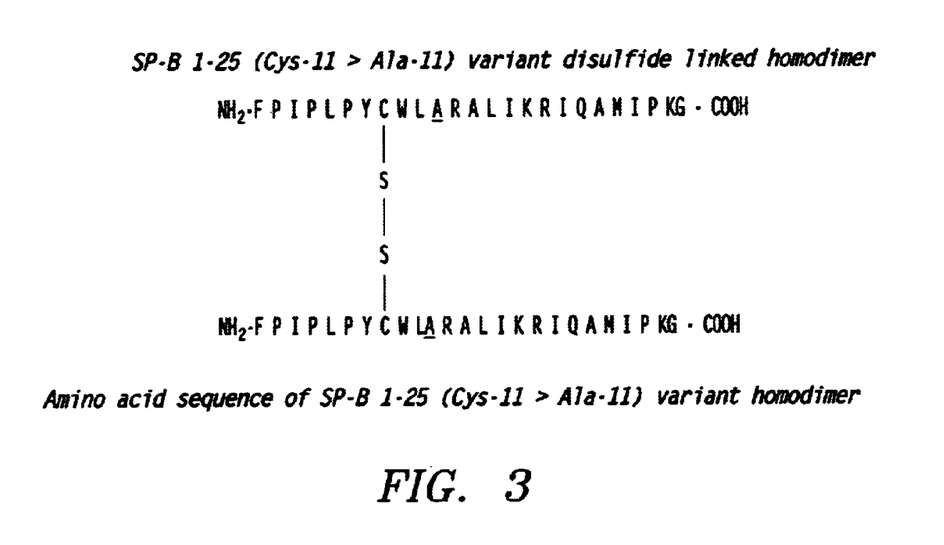
FIG. 3 is the amino acid sequence in one letter code of the SP-B1–25 Cys 11→Ala 11variant disulfide linked homodimer SEQ ID NO:4 of the present invention.

The invention is a new synthetic SP-B peptide analog that may be used as a component of a pharmaceutical composition comprised of a surfactant-peptide dispersion for RDS therapy. In a preferred embodiment, the SP-B1–25 dimer (SEQ ID NO:2) is synthesized by covalently linking N-termninal domains of human SP-B that comprise selected active sites of the protein with a variable sized spacer that links an amino acid (Cys 8 in the preferred embodiment) of one peptide monomer to another amino acid (Cys 8) of the second peptide, as in FIG. 3 (see e.g. SEQ ID NO:3). These covalently linked peptides form a dimer that mimics a portion of the secondary structure of native SP-B, thus retaining the desirable biological activities of native pulmonary surfactant. The dimer comprised of N-terminal fragments may have substantially the same amino acid sequences as the native composition, or may be a variant thereof (see e.g., the Cys 11→Ala 11 variant of FIG. 3—SEQ ID NO:4) and is smaller than the full-length native protein due to a truncation from the C-terminal end. Like native SP-B, the amino acid sequence and intramolecular linking of the dimer of the invention are designed to enhance formation of a peptide-lipid network in vivo, i.e., at the air/liquid interface of the lung, that enhances the existence of buckled and flat monolayers and lowers surface tension as observed in the native protein.

Figure 2:
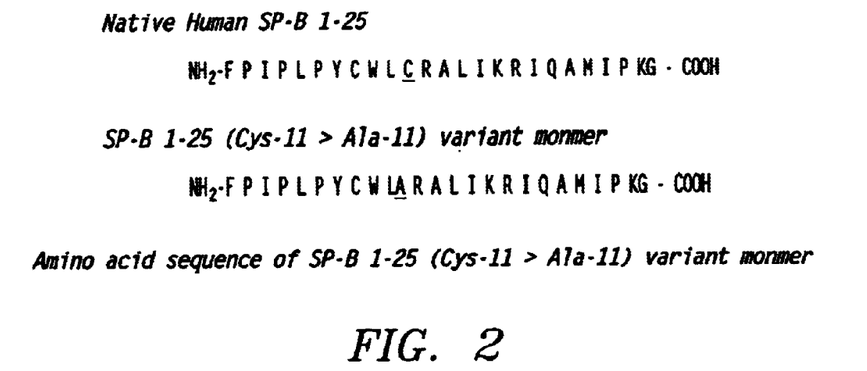
FIG. 2 is the amino acid sequence in one letter code of SP-B1–25 of native human SP-B1–25 SEQ ID NO:2 and the Cys 11→Ala 11 variant monomer SEQ ID NO:3.

The composition of the invention possesses certain properties that are superior to both native human SP-B and naturally derived surfactant therapies. Unlike the proteins extracted from animal tissue, the proposed method of synthesizing the surfactant minimizes the risk of contamination by other compounds and microorganisms. The method also is more economic as compared to isolating native and recombinant SP-B. The SP-B1–25 dimer is less water-soluble and more surface active than other SP-B peptides, such as the SP-B monomer (See FIG. 2), which leads to better retention of the dimer at the alveoli membrane interface. The SP-B1–25 dimer also has an enhanced shelf life and is highly resistant to lung surfactant inhibitors.

Figure 1:
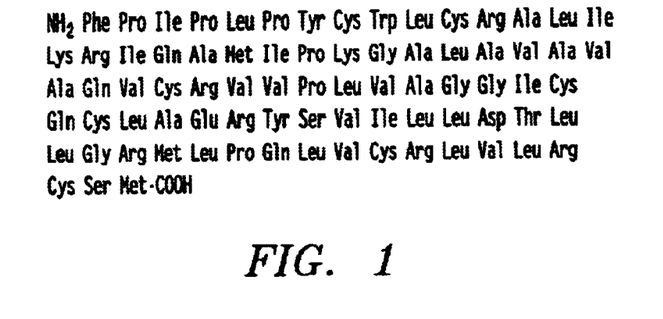
FIG. 1 is the amino acid sequence in three letter code of native human surfactant protein B (SP-B) SEQ ID NO: 1.

The compositions of the present invention are prepared by using a standard synthesis procedure according to the amino acid sequence of native SP-B as seen in FIG. 1 (SEQ ID NO: 1). As noted above, native human SP-B is a constituent of pulmonary surfactant-associated proteins that promote alveolar stability by lowering surface tension at the air-liquid interface in the peripheral air spaces of the lung. Native SP-B protein is a 17k Da dimeric protein produced by the alveolar type II cells and is formed from a 381 amino acid precursor. Human SP-B (SEQ ID NO:1) is a 79 residue polypeptide, although certain published reports place the total length within the range of 78–80 residues. Native SP-B has a C-terminal methionine and contains seven cysteine residues. Human SP-B has three intrachain disulfide bridges, linking $Cys^8$ to $Cys^{77}$, $Cys^{11}$ to $Cys^{71}$, and $Cys^{35}$ to $Cys^{46}$. In its native form, the human SP-B subunit exists as a disulfide-linked homodimer having a interchain disulfide bridge at $Cys^{48}$. In native SP-B, the disulfide-mediated interaction between remote regions of the native polypeptide have an undetermined result on the conformational state of both the N- and C-terminal regions.

SP-B's main function is to lower the surface tension by inserting lipids into the air/liquid interface of the lung and SP-B has been observed to increase the rate of spreading of surfactant from the aqueous phase to a phospholipid monolayer along the air water interface of the alveolus, partially by destabilization of the lipid bylayer. SP-B has a frequency of intermittent, highly-charged residues, including both hydrophylic and hydrophobic regions. The interrelationship between hydrophilic and hydrophobic regions causes stabilization of a phospholipid layer which resists the tendency of alveolar collapse.

Pursuant to the present invention, a peptide analog of the known SP-B primary sequence is synthesized by covalently linking constituent N-terminal SP-B residues 1–25 with a variable size spacer, preferably a disulfide link. The resulting peptide analogs interact with lung membranes and have the same secondary conformation as the native SP-B peptide contained in pulmonary surfactant-associated lipids. The peptide-lipid network formed in the surfactant lipids by administering the SP-B1–25 dimer of the present invention enhances the co-existence of buckled and flat monolayers in the same fashion as the native SP-B protein. Also, the SP-B1–25 dimer optimizes the microstructure of surfactant dispersions by inducing a network of peptide-rich domains in surfactant lipid mono-and biolayers that yield buckled molecular structures that enhance the reversible spreading of the dispersion, as can be demonstrated both in vivo and in vitro. However, because the SP-B1–25 dimer is less water soluble and more surface active than the native peptide, the protein analogs of the invention exhibit superior biochemical properties including solubility and retention at the air-liquid interface, and higher activity.

Pharmaceutical compositions of the present invention are formulated and stored by known aseptic techniques and may contain physiologically compatible carriers or solvents and preferably contain between 95% and 98.5% lipids by weight percent in addition to the peptide analog of SP-B described herein. Suitable lipids include dipalmitoylphosphatidylcholine (DPPC), phosphatidylcholine (PC), cardiolipin (CL), phosphatidyl glycerol (PG), phosphatidyl serine (PS), fatty acid (FA), and triglyceride (TG). PC comprises approximately 80% of the phospholipids, about 40–50% of which is DPPC. The remaining lipids are present in minor concentrations.

When formulated in a liquid the lipids composition may be approximately 25 mg lipids/ml and may include ovine or bovine SP-C. The formulation may include liposomes, manufactured by conventional means, and may incorporate antioxidants or other therapeutic agents and may include diagnostic products such as imaging agents.

EXAMPLE 1

Solid Phase Synthesis Purification and Characterization of the SP-B1–25 Cys 11→Ala 11 Variant Monomer The SP-B1–25 monomer (SEQ ID NO:2), of which the present invention is comprised, may be synthesized by known chemical techniques. (Glasser, et al., Proc. Natl. Acad. Sci. U.S.A. 84:4007, 1987 Jacobs, et al., J. Biol. Chem. 262:9808, 1987; Floros, et al., J. Biol. Chem. 261:9029, 1986; White, et al., Nature 317:361, 1985; Whitsett, et al., Pediatr. Res. 19:501, 1985; Warr, et al., Proc. Natl. Acad. Sci. U.S.A. 84:7915, 1987; Hawgood, et al., Proc. Natl. Acad. Sci. U.S.A. 84:66, 1987; Glasser, et al., J. Biol. Chem. 263:9, 1988, Glasser, et al., supra, J. Biol. Chem. 263: 10326, 1988; and Jobe et al., Am. Rev. Resp. Dis. 136:1032, 1987). Preferably, however, the SP-B1–25 monomer peptide (FIG. 2) is synthesized on a 0.25 mmol scale with an Applied Biosystems model 431 A peptide synthesizer using a FastMoc™ strategy. Fields, C. G., Lloyd, D. H. Macdonald, R. L., Ottenson, K. M., and Noble, R. L. 1991. "HBTU Activation for Automated Fmoc Solid-Phase Peptide Synthesis," Peptide Res. 4:95–101. The peptides are synthesized with prederivatized Fmoc-Gly resin (Calbiochem-Nova, La Jolla) or PEG-PA resin (Perceptive Biosystems, Old Connecticut Path, Mass.) and are single coupled for all residues.

Figure 4:
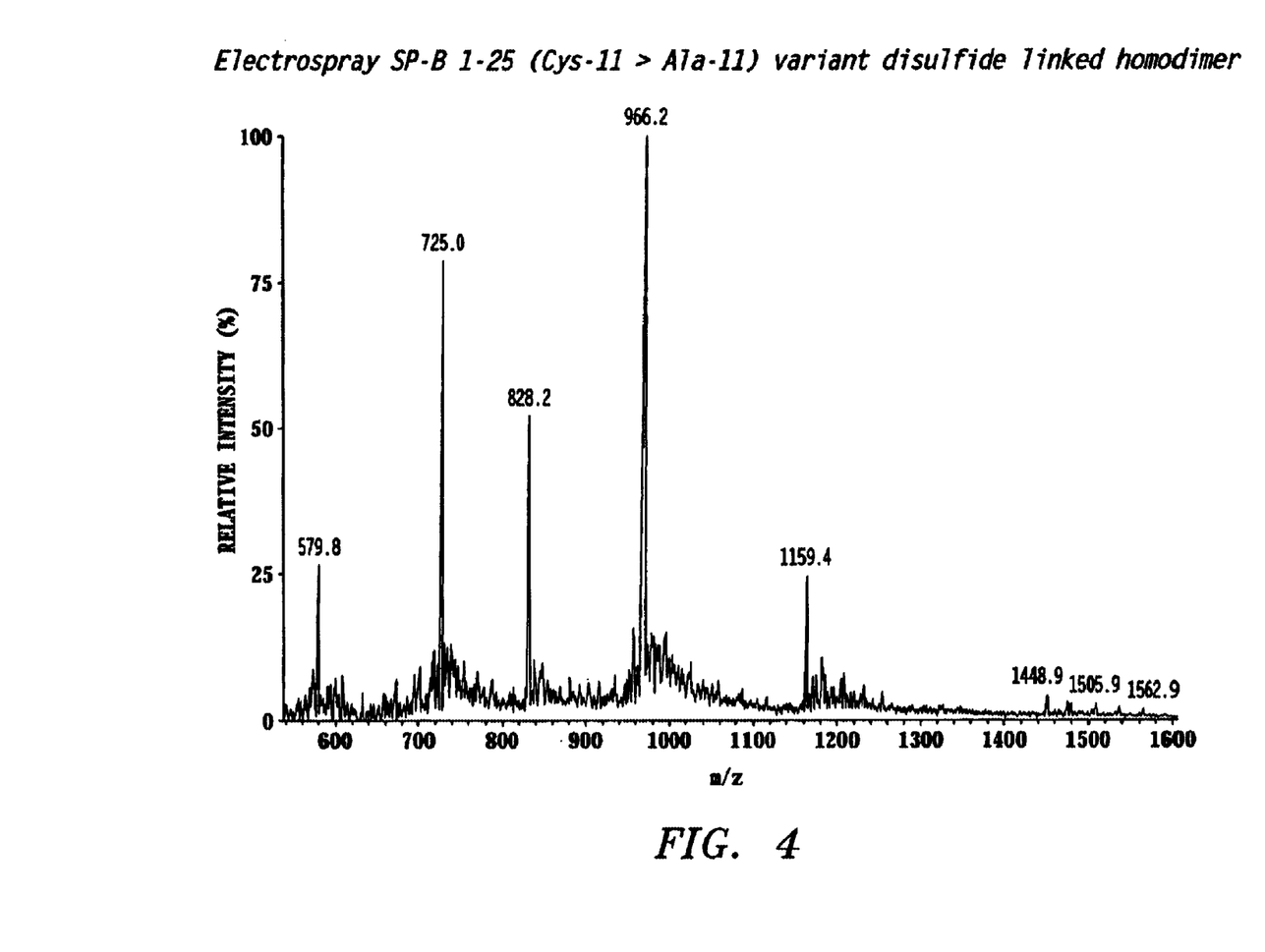
FIG. 4 is a fast atom bombardment electrospray mass spectrograph of the SP-B1–25.

Purification of crude peptide product is by reverse-phase High Performance Liquid chromatography with a Vydac reverse phase C8-column (Vydac, Hesperia, Calif. using a linear gradient of water:acetonitrile (0 to 100% acetonitrile with 0.1% trifluoroacetic acid as anion pairing agent) over a period of one hour. Purified peptide is twice freeze dried at a concentration of 5 mg peptide/ml from acetonitrile: 10 mM HCl solutions to remove acetate counterions that interfere with activity, and in vivo—in vitro measurements. The molecular mass of the monomeric SP-B1–25 peptide is confirmed by fast atom bombardment electrospray mass spectroscopy (See FIG. 4). The complete sequence of the human SP-B manomer may be determined by reference to the Protein Data Bank—PDB—IDFW. The sequence of non-human mammalian SP-Bs may be determined by conventional means and the synthesis of the peptide analog of the invention based on the mammalian sequence.

EXAMPLE 2

Formulation of the SP-B1–25 (Cys-11 →Ala-11) Variant Disulfide Linked Homodimer of the Present Invention The SP-B1–25 (Cys-11→Ala-11) variant monomer (SEQ ID NO:3) is first reduced with 100 mM DDT (dithiothreitol) in TFE (trifluoroethanol): 10 mM sodium phosphate buffer pH 7.5 (1: 1, v:v) at a concentration of 1 mg peptide per ml solution for 12 hours prior to oxidation. The peptide solution is then passed through a Sephadex P-10 size exclusion column using TFE (trifluoroethanol): 10 mM sodium phosphate buffer pH 7.5 (1: 1, v:v) to remove reducing agent prior to oxidation—disulfide formation. The isolated peptide solution is then freeze-dried overnight to remove solvent. The dry peptide powder is dissolved in TFE (trifluoroethanol):10 mM sodium phosphate buffer pH 7.5 (1: 1, v:v) at a concentration of 1–2 mg peptide/ml and stirred vigorously for 24 hours to facilitate the air-mediated oxidation of the SP-B1–25 (Cys-11→Ala-11) variant monomer to form a Cys8-Cys8 disulfide linked SP-B1–25 (Cys-11→Ala-11) variant disulfide linked homodimer (SEQ ID NO:4). The molecular mass of the monomeric SP-B1–25 peptide is confirmed by electrospray mass spectroscopy (FIG. 4) and indicates that the yield of dimeric product to be essentially 100%. The homodimer peptide is then freeze-dried to remove the organic solvent prior to formulation with lipid.

Alternative SP-B1–25 monomer (SEQ ID NO:2) can be produced by know recombinant DNA techniques (Sambrook et al., Molecular Cloning: A laboratory Manual 1989; see also review of recombinant biology in Methods in Enzymology, vol 185, Goeddel, D. V., ed, 1990; Towbin JA, Herz 18:213–221, 1993). This technology allows directed synthesis of a protein in host cells that normally do not express the selected protein. To produce recombinant monomeric SP-1–25 protein, cells are transfected with an expression vector containing the DNA encoding the mammalian monomer SP-B25. Under appropriate growth conditions, the transformed host cell synthesize the SP-B1–25 polypeptide, which can be isolated from the cells or from growth medium.

A wide variety of host cells are available for use in recombinant technology. Host cells suitable for the recombinant production of monomer SP-B1–25 comprise prokaryotic cells such as strains of *E. coli*, Bacillus or Pseudomonas (Kung, H.-F., M. Boublik, V. Manne, S. Yamazaki and E. Garcia, Curr. Topics in Cell. Reg. 26: 531–542, 1995) or unicellular eukaryotic cells as yeast *Saccharomyces cerevisiae* (Bemis, L. T., F. J. Geske and R. Strange, Methods Cell Biol., 46: 139–151, 1995). Host cells for recombinant production may also be derived from multicellular eukaryotes comprising invertebrates as insects (*Spodoptera frugiperda* Sf9 cells) (Altmann F., E. Staudacher, IB Wilson, and L Marz, Glycoconj J., 16: 109–123,1999) and vertebrate cells, including numerous mammalian cell lines comprising mouse fibroblasts, chinese hamster ovary cells (CHO/-DHFR)(Urlaub and Chasin, P.N.A.S. 77:4216, 1980), baby hamster kidney (9BHK, ATCC CCL 10); monkey kidney CV1 line transformed by SV40 (COS-7, ATCC CRL 1651) and human embryonic kidney cell line 293 (Tartaglia etal., P.N.A.S. 88: 9292–9296, 1991 and Pennica et al., J.. Biol. Chem. 267: 21172–21178, 1992).

While bacteria and yeast have been standard recombinant host cells for over a decade, investigators have recently transformed cells from higher plants to express human recombinant proteins as antibodies (Hiatt, A. T. and J. K. Ma, Int. Rev. Immunol., 10: 139–152, 1993) and hemoglobin (Theisen, M. in Chemicals Via Higher Plant Bioengineering, F.Shahidi et al., eds, Plenum Publishers, NY, p. 211–220, 1999). Plant biotechnology offers many advantages for efficient production of heterologous polypeptides, and this approach may be useful for production of monomer SP-B1–25 (see also Plant Technology:

New Products and Applications, John Hammond, et al., eds., Springer, N.Y., 1999). The appropriate choice of host cell is determined by what is efficient and required for the accurate expression, processing and recovery of monomer SP-B1–15.

The expression vector for production of recombinant monomer SP-B1–25 (SEQ ID NO:2) is constructed by inserting into a chosen vector the DNA encoding SP-B1–25 and any nucleic acid sequences required for its propagation, expression and recovery from the host cell. These sequences comprise a replication origin, selection marker, promoter, ribosome binding site, enhancer sequences, RNA splice sites, transcription termination sites, and any sequence necessary for targeting, expression and recovery. The nucleic acids are inserted into the vector using standard recombinant DNA techniques (Sambrook et al, 1989). If amplification is necessary, the techniques for polymerase chain reaction (PCR) are clearly described (Innis, et al., Biotechnology 24:6–10, 1992).

A variety of expression vectors, comprising plasmids, phage particles, retroviruses or simply a genomic insert, are readily available that would be appropriate for the expression of a polypeptide such as monomer SP-B1–25 (SEQ ID NO:2) in the chosen host cell system. For example, expression vectors are described for *E. coli* (Shatzman, A. R. and M. Rosenberg, Ann. N.Y. Acad. Sci., 840: 233–248, 1998), yeast (Bemis, supra. 1995), and mammalian cells (Werner, RG, W. Noe, K. Kopp and M. Schluter, Arzneimitt. 48:870–880, 1998). For plants, Ti plasmids are delivered by Agrobacterium infection and viral vectors are also available (Hansen, G. and M. D. Chilton, in Plant Technology: New Products and Applications, H. Hammond et al., eds., Springer, p. 22–57, 1999). Verma et al. (J. Immunol. Methods, 216: 165–181, 1998) and Morrison (Ann. Rev. Immunol.10: 239–265, 1992) discuss the relative advantages and disadvantages of various expression systems for the recombinant production of human proteins. In the appropriate expression system, the recombinant monomer SP-B1–25 can be synthesized and then isolated either from host cells or from the growth medium. Monomer SP-B1–25 is purified to homogeneity as described for chemically purified peptide, with modifications as required for the expression system selected.

EXAMPLE 3

Formulation of a Therapeutic Composition Containing the SP-B1–25 Dimer (Cys 11→Ala-11) Variant Disulfide Linked Homodimer and Synthetic Surfactant Lipid Dispersions The SP-B1–25 dimer of the present invention may be formulated in a biocompatible composition containing synthetic surfactant lipid dispersions for administration to a human patient to treat respiratory disorders, including particularly respiratory distress syndrome. Preferably, SP-B1–25 (Cys11→Ala-11) variant disulfide linked homodimer (SEQ ID NO:4) is formulated with synthetic surfactant lipids by co-solvating the peptide (3% by wt) with synthetic surfactant lipids in chloroform:methanol (1:1, v:v). The synthetic surfactant lipid dispersion composition is DPPC (dipalmitoyl phosphatidycholine), has POPG (1-palmitoyl-2-oleoyl phosphatidyl glycerol):PA (palmitic acid) (66:22:9, wt %) (16) and has a final concentration of 25 mg lipids/ml PBS (phosphate buffered saline). The chloroform-methanol-lipid peptide solution in a 20 ml screw cap vial is dried under nitrogen gas at 25° C. and stored in the refrigerator at 5° C. for 12 hours to cure (form a gel-like suspension). The cured lipid-peptide dispersion is then freeze-dried to remove the aqueous solvent and rehydrated with Milli-Q grade water followed by two more cycles of heating, low-temperature curing, and freeze-drying before final hydration and storage at 5° C. to use.

EXAMPLE 4

Determination of the Secondary Structure of the SP-B1–25 (Cys-11→Ala- 11) Variant Disulfide Linked Homodimer (SEQ ID NO:4).

Circular Dichroism (CD) measurements are made with an AVIV 62DS spectropolarimeter (AVIV Associates, Lakewood, N.J.). The AVIV 62DS is fitted with a thermoelectric temperature controller and the sample temperature maintained at 25° C. Peptide-solvent solutions are measured in 0.1 mm light path demountable cells scanned from 250 nm to 195 nm at a rate of 10 nm/min and a sample interval of 0.2 nm. The instrument is routinely calibrated with (+)-10-camphorsulfonic acid (1 mg/ml) and a 1-mm path length cell (Johnson, 1990 Johnson, W. C. J. 1990, "Protein Secondary Structure and Circular Dichroism: A Practical Guide." Proteins Struct. Funct. Genet. 7:205–214, and the ellipticity expressed as the mean residue ellipticity, $\theta_{MRE}$ (deg cm$^2$ dmol$^{-1}$). Peptide sample concentrations are determined by quantitative amino acid analysis (UCLA Micro Sequencing Facility, Los Angeles, Calif. The percentage of α-helix conformation in the peptide is estimated using the formalism of Chen et al. Chen YH, Yant JT, Chaus KH. 1974. "Determination of the Helix and β Form of Proteins in Aqueous Solution by Circular Dichroism." Biochemistry 13:3350–3359. This approach assumes the maximum theoretical ellipticity for a given peptide or protein at 222 nm may be derived from the number of amino acid residues n, and the ellipticity at 222 nm of a helix of infinite length described by Equation (1).

$$\% \; \alpha\text{-helix} = \theta_{MRE222}[-39{,}500(1-(2.57/n))] \text{deg cm2 dmol-1} \quad (1)$$

Figure 5:
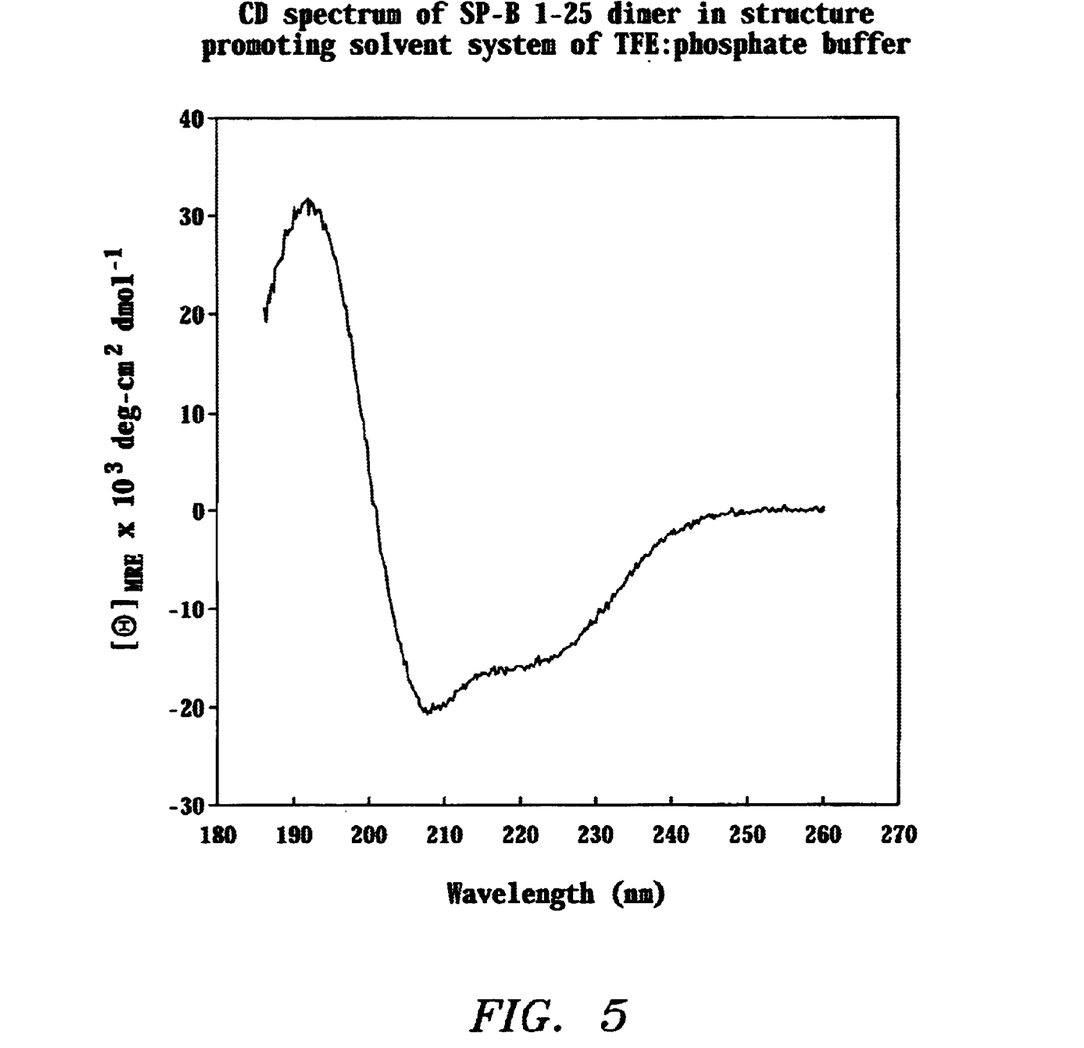
FIG. 5 is a Circular Dichroism (CD) spectrum of SP-B1–25 dimer in a structure promoting solvent system of trifluoroethanolamine (TFE):phosphate buffer.

The secondary structure of the SP-B1–25 (Cys-11→Ala-11) variant disulfide linked homodimer is accessed in two different structure promoting membrane mimic environments using Circular Dichroism spectroscopy. In TFE:phosphate buffer, 1: 1, v:v (FIG. 5), a solvent system used to mimic membrane associating peptides and proteins, the SP-B1–25 dimer had a spectral dichroic minima at 222 and 208 nm and a dichroic maximum near 193 nm typical of a peptide having a dominant helical content. Using the formalism of Chen et al. (1974 supra), the spectral figure at 222 nm suggests the peptide assumed about 41% helical conformations.

Figure 6:
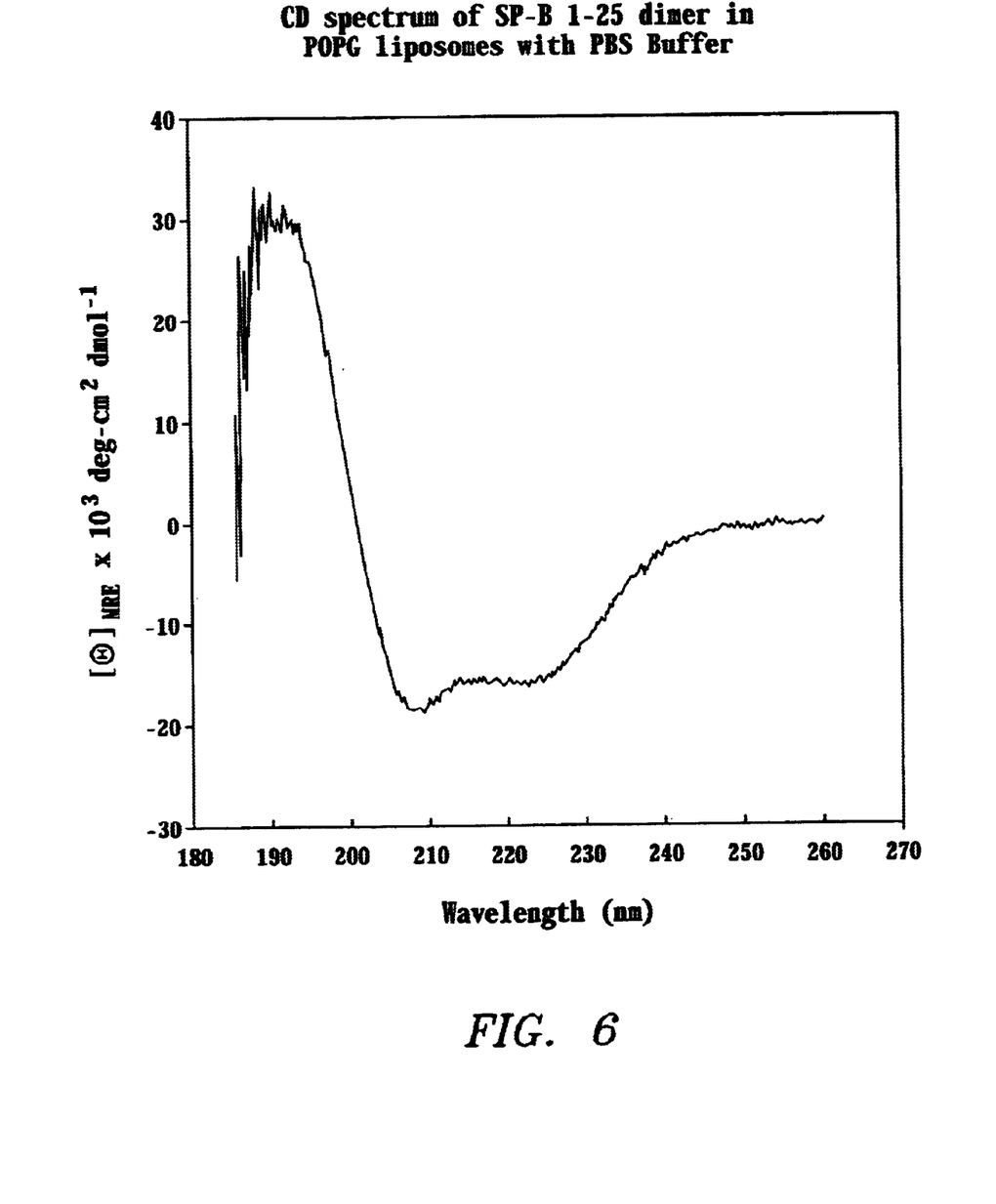
FIG. 6 is a CD spectrum of SP-B1–25 dimer in palmitoylolsoyl phosphatidyl glycerol (POPG) liposomes with phosphate buffered saline (PBS) palmitoyl olcoyl phosphatidyl glycerol buffer.

Referring to FIG. 6, when the peptide is added to POPG liposomes (a major lipid component of surfactant lipid) the helical component is similar to that observed in the organic solvent system. Deconvolution of the spectra using the computer program suggests that the peptide assumed about 44.7% helix, 17.1% beta sheet, 28.2% beta turn and 10.0% disordered conformations in POPG surfactant lipid liposomes and are typical of the conformations observed for native proteins in organic solvent/water mixtures and synthetic SP-B peptides in this type of environment. [Lincomb Perczel, A., Park, K., Fasman, G. D., Analysis of the circular dichroism spectrum of proteins using the convex constraint algorithm: A practical guide. Analytical Biochem 203:83–93, 1992] [Compare Perez-Gil, J., A. Cruz, Casals, C. Solubility of hydrophobic surfactant Structural studies on SP-B and SP-C in aqueous organic solvents and lipids. Biochim. Biophys Acta, 1168:261–270, 1993; Bruni, R., Taeusch, W., and Waring, A., "Surfactant protein SP-B: Lipid interactions of synthetic peptides representing the amino terminal amphipathic domain," Proc. Nat. Acad. Sci. USA, 88:7451–7455 (1991); Gordon, L. M., Horvath S., Longo, M., Zasadzinski, J. A. N., Taeusch, H. W., Faull, K., Leung, C., and Waring, A. J., "Conformation and molecular topography of the N-terminal segment of surfactant protein B in structure-promoting environments," Protein Science 5:1662–1675 (1996)].

EXAMPLE 5

Synthesis of Analogs or Derivatives of the SP-B1–25 Dimer Using the Molecular Design Rationale of the Present Invention Although the preferred embodiment of the present invention has been described as the SP-B1–25 Cys 11→Ala-11 variant Cys8—Cys8 disulfide linked homodimer (SEQ ID NO:4), various derivatives or functional analogues thereof may be prepared without departing from the spirit of the invention. These derivatives or functional analogues may be designed according to the rationale of the present invention as described herein.

Selection of an N-terminal segment of a mammalian SP-B protein as the basis for a therapeutic composition is based on the capability of the N-terminal segment to mimic many of the in vitro—in vivo functions of the full-length SP-B protein. However, the N-terminal segment may lack the respreadability of lipids observed with the full length protein and, in addition, may exhibit some hemolytic activity not seen with full length SP-B. Therefore, pursuant to this invention, several modifications may be made in both the primary sequence and the tertiary structure. For example, emulation of the Saposin fold amphipathic helix-disulfide connectivity unique to the Saposin protein family including SP-B, Saposins, NK-lysin, Granulysin, Amoebapore, of the N-terminal segment to make it more closely emulate the in vitro-in vivo structure and function of the native SP-B proteins. [Liepinish, E., Andersson, M., Ruysschaert, J.-M., and Otting, G. (1997) "Saposin Fold Revealed by the NMR Structure of NK-Lysin.": Nature. Struct. Biol. 4:793–795; Waring, A. J., Chen, Y., Faull, K. F., Stevens, R., Sherman, M. A., and Fluharty, A. L. , "Porcine Cerebroside Sulfatide Activator Protein (SAP-B) Secondary Structure: CD, FTIR, and NMR Studies,: Molecular Genetics and Metabolism 63:14–25 (1998).]

In the preferred embodiment herein, Cys-11was replaced with alanine (Cys surrogate residue SP-B (Cys-11→Ala-11) variant monomer) so as to provide a possible disulfide linkage at Cys-8 to a second SP-B1–25 (Cys-11→Ala-11) variant having a single Cys-8, forming a unique SP-B1–25 (Cys-11→Ala-11) variant disulfide linked homodimer (FIG. 3) (SEQ ID NO:4). Additional structural/functional relationships should be accommodated when synthesizing the N-terminal SP-B analogs of the present invention. For example, the resulting pharmaceutical formulation comprised of an N-terminal SP-B analog must be capable of maintaining a coherent, tightly packed monolayer that avoids alveolar collapse during expiration. Accordingly, positively charged residues in the SP-B analog may lead to higher collapse pressures and lower surface tensions. See Longo, M. L., Bisagno, A. M., Zasadzinski, J. A. N., Bruni, R. and Waring, A. J., A Function of Lung Surfactant Protein SP-B, Science 261:453–456, Jul. 23, 1993.

Similarly, the secondary conformations and surface activities of SP-B analogs or derivatives should correlate to an α-helical structure that maintains the ability of the peptide to interact with lipids and with the surface activity of peptide/lipid dispersions. Amino acid substitutions that alter either the charge or the hydrophobicity of the analog tend to lower the helical content and reduce the association of the N-terminal segment with the lipid dispersion. See Bruni, R., Taeusch, H. W., and Waring, A. J., Surfactant protein B: Lipid interactions of synthetic peptides representing the amino-terminal amphipathic domain, Proc. Natl. acad. Sci. USA 88:7451–7455, August 1991. Generally, SP-B analogs should be designed to optimize their fumction in accord with the native SP-B protein based on topography, charge distribution, contribution and physical or chemical properties as described in Gordon, L. M., Horvath, S., Longo, M. L., Zasadzinski, J. A. N., Taeusch, H. W., Faull, K., Leung, C., and Waring, A. J., Conformation and molecular topography of the N-terminal segment of surfactant protein B in structure-promoting environments, Protein Science, 5:1662–1675, 1996.

With respect to the length of the molecule synthesized pursuant to the present invention, from the N-terminal end, the peptide analog of this invention is shorter than the native 79 residue peptide chain. The SP-B1–25 homodimer is one example of a molecule that is shorter than the native protein, but that retains the critical function as described herein. Other N-terminal molecules may be created by truncation from the C-terminal end with preservation of the functional properties described above. Therefore, the invention contemplates molecules from between approximately 25 to 77 residues, preferably formed as a homodimer, and all integral values between 25 and 77. Specifically, with respect to α-helicity, other molecules having a length between 40 and 50 may yield a conformation preserving the function of the native SP-B protein.

Therefore, other modifications in accord with the foregoing rationale may be made pursuant to this invention to create other SP-B N-terminal segment analogs or derivatives, particularly homodimers, to achieve both the benefits of the N-terminal fragment described herein and the physical and chemical properties of the native protein.

EXAMPLE 6

Results of Administration of the SP-B1–25 Dimer in an Animal Model of Acute Respiratory Distress Syndrome To demonstrate the advantages of the preferred formulation of the present invention compared to an N-terminal monomer described in the literature (Gordon, L. M., Horvath, S., Longo, M., Zasadzinski, J. A. M., Taeusch, H. W., Faull, K., Leung, C., and Waring, A. J., "Conformation and Molecular Topography of the N-terminal segment of Surfactant Protein B in Structure-Promoting Environments, Protein Science 5:1662–1675 (1996)), a commercially available pharmaceutical composition for respiratory disorders (Survanta®) and a phospholipid surfactant, comparative animal studies of lung function were conducted in mature lavaged rat lung and preterm rabbits.

The experimental surfactant preparations were prepared by mixing synthetic peptides into a standard phospholipid mixture (PL) consisting of dipalmitoyl phosphatidylcholine (DPPC), 1-palmitoyl,2-oloeyl phosphatidylglycerol (POPG), and palmitic acid (PA) (DPPC:POPG:PA=7:2:1 wt/wt/wt), creating: PL+3% monomeric SP-B1–25 (B1–25 monomer) and PL+3% dimeric SP-B1–25 (B1–25 dimer).

The phospholipids and the synthetic peptide(s), stored in chloroform, were freeze-dried, added together, and the mixture was then rehydrated in 0.15 N NaC 1 over 48 h with gentle stirring at 37° C. The clinical surfactant Survanta®, containing phospholipids with SP-B and SP-C, was used as a standard. All surfactant preparations were prepared at a concentration of 25 mg of phospholipids/mL and administered in a dose of 100 mg of phospholipids/kg of body weight.

Rats were anesthetized with 35 mg/kg of pentobarbital sodium and 80 mg/kg of ketamine by intraperitoneal injection. After placement of a tracheal cannula, the rats were supported on a rodent ventilator (Harvard Apparatus, South Natick, Mass.) with 100% oxygen, a tidal volume of 7.5 mL/kg and a rate of 60/min. An arterial line was placed in the abdominal aorta for serial measurements of arterial blood gases and the rats were paralyzed with 2 mg/kg of pancuronium bromide intravascularly. Only animals with $PaO_2$ values >400 Torr while ventilated with 100% oxygen were included in the experiments. The lungs were gently lavaged 8–12 times with 8 mL of 0.9% NaCl warmed to body temperature until the $PaO_2$ in 100% oxygen had reached stable values of less than 100 Torr, at which time they were treated with 100 mg/kg of surfactant (time=0 min). Arterial blood gases, tidal volume, peak inspiratory pressure (PIP), and positive end-expiratory pressure (PEEP) were determined at 15 minute intervals throughout the experiment.

After 2 hours of ventilation, the rats were sacrificed with the intramuscular administration of 100 mg/kg pentobarbital sodium and exsanguination and the lungs were degassed in situ. A pressure-volume curve was measured in situ in each pair of rat lungs to define lung mechanics: Lungs were inflated and deflated using a bidirectional Harvard pump coupled to a 50-mL glass syringe, and pressure was continuously recorded on a Gould multichannel recorder. Each pressure-volume curve was corrected for the compliance of the system by subtracting the pressure-volume curve of the pump-syringe unit carried out before each curve. Absence of air leaks was assessed by verifying that lung volumes changed less than 0.1 mL/min over 3 minutes at 30 cm $H_2O$ pressure. The lung volume measured at a pressure of 5 cm $H_2O$ ($V_5$) was issued as an index of stability at low lung volumes, whereas lung volumes at a pressure of 30 cm $H_2O$ ($V_{30}$) were assumed as total lung capacity. Each treatment group consisted of 8 animals. All experiments were performed humanely and with the approval of the Animal Care and Use Committee of the Harbor-UCLA Medical Center Research and Education Institute. The arterial/Alveolar $PO_2$ (a/A) ratio was calculated using the $PaO_2$ $PaCO_2$, and $FiO_2$ values and used to express oxygenation. Oxygenation and data from the pressure-volume curves are given as mean±SEM with 8 rats in each experimental group.

Figure 7:
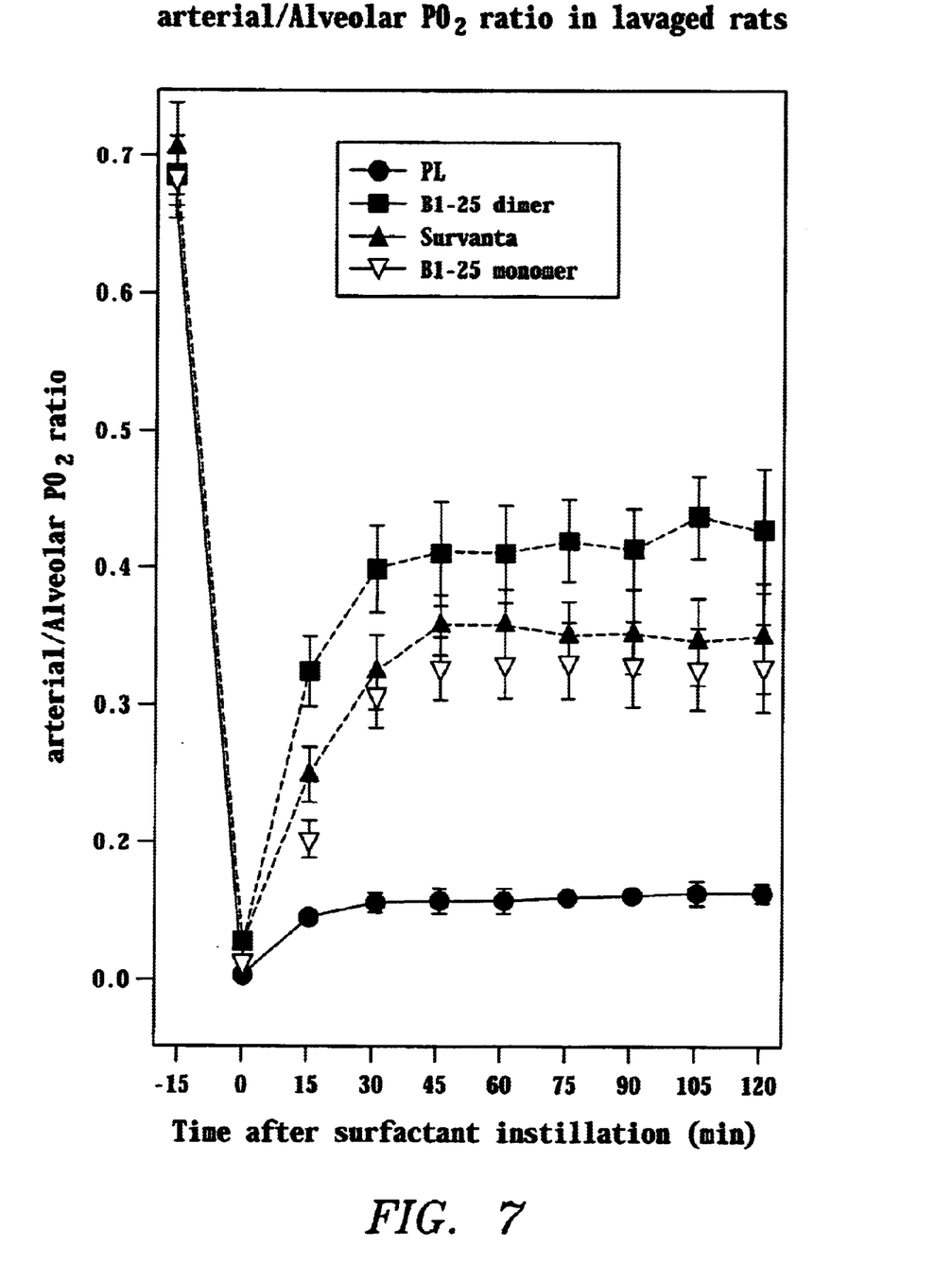
FIG. 7 is a measurement of oxygenation in lavaged rat lungs comparing a standard phospholipid mixture (PL) -●-, Survanta -▲-, the SP-B1–25 monomer -▽-, and the SP-B1–25 dimer of the present invention -■-.

Groups of 8 rats were lavaged until surfactant-deficiency and were than treated with one of 4 surfactant preparations, i.e., PL, B1–25 dimer, B1–25 monomer, or Survanta®. Rats treated with B1–25 dimer surfactant reached the highest oxygenation values (arterial/Alveolar $PO_2$ ratios) and rats treated with PL the lowest (FIG. 7). The surfactant preparations could be ranked as follows: B1–25 dimer >Survanta®>B1–25 monomer >PL surfactant.

Figure 8:
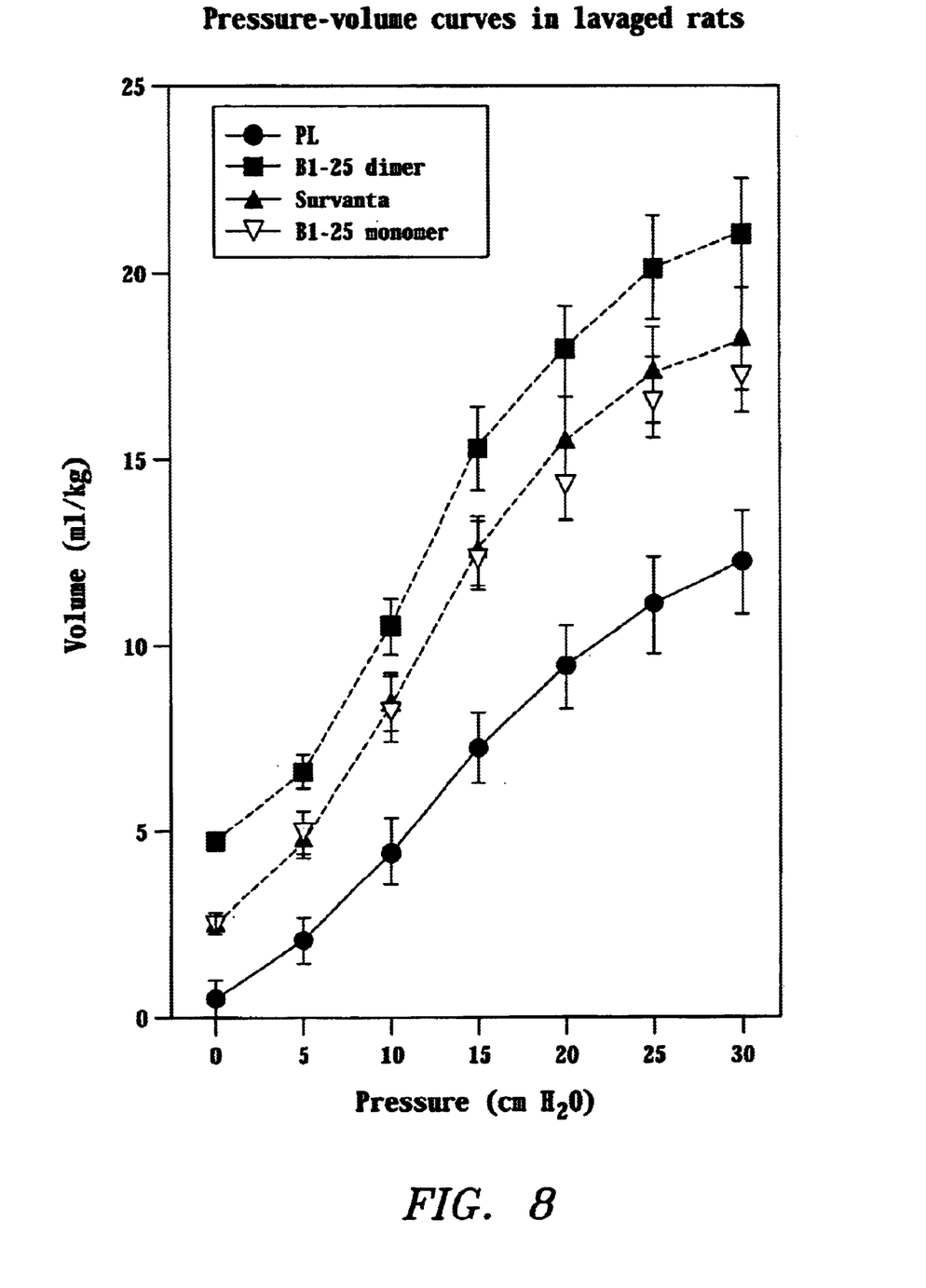
FIG. 8 is a measurement of lavaged rat lung volume as a function of pressure comparing a standard phospholipid mixture (PL) -●-, Survanta -▲-, the SP-B1–25 monomer -▽-, and the SP-B1–25 dimer of the present invention -■-.

The group of rats treated with B1–25 dimer surfactant had the largest lung volumes on the postmortem pressure-volume curves, followed by those treated with Survanta®, B1–25 monomer, and PL surfactant (FIG. 8). All values are expressed as means±standard error (SEM).

In a comparative study of lung function in preterm rabbits, the experimental surfactant preparations were prepared as described above for lavaged rats. Pregnant New Zealand White rabbits were preanesthetized at 27 day gestational age with 50 mg/kg ketamine and 5 mg/kg acepromazine by intramuscular injection and then given general anesthesia with 50 mg/kg ketamine intravenously prior to undergoing a cesarean section. Fetuses were sequentially delivered, weighed, and anesthetized with an intraperitoneal injection of a mixture of 10 mg/kg ketamine and 0.1 mg/kg acepromazine. The trachea of each newborn was exposed through a small incision in the anterior neck, and a short tube from an 18-gauge needle was tied in the trachea. Each rabbit was ventilated with 100% oxygen using an anesthesia bag and manometer for about five breaths and transferred to a temperature-controlled ventilator-plethysmograph system that permits the simultaneous ventilation of 10 newborn rabbits. The plethysmographs are a serial of 10 clear Plexiglas-boxes, temperature-controlled at 37° C., that are connected to 10 rebreathing circuits containing soda lime and driven by a Sechrist infant ventilator (Sechrist Industries, Anaheim, Calif.). The rabbits were ventilated with 100% oxygen at a rate of 40 breaths/minute with a 1:1 inspiratory-to-expiratory time ratio. No positive end-expiratory pressure was used to avoid the air trapping that seems to occur in preterm rabbits. The initial peak inspiratory pressure was 30 cm $H_2O$ and peak pressure was adjusted individually to achieve a tidal volume of about 10mL/kg as measured with a pneumotachometer (Validyne, Northridge, Calf.) and a multichannel recorder (Gould Inc., Cleveland, Ohio). Peak inspiratory pressure was limited at 35 cm $H_2O$ to avoid pneumothorax. Dynamic compliance was calculated by dividing tidal volume by peak inspiratory pressure and the body weight in kg (mL/kg/cm $H_2O$) and monitored every 15 minutes.

All preterm rabbits were treated with 100 mg/kg of an experimental surfactant after insertion of the endotracheal tube and prior to bagging. After 60 minutes of ventilation, each rabbit was sacrificed by an administration of an intrathecal injection of lidocaine and was disconnected from the ventilator. Pressure-volume curves were measured in situ to define lung mechanics. Lungs were inflated and deflated using a bidirectional Harvard pump coupled to a 10-mL glass syringe, and pressure was continuously recorded on a Gould multichannel recorder. Each pressure-volume curve was corrected for the compliance of the system by subtracting the pressure-volume curve of the pump/syringe unit carried out before each curve. Absence of air leaks was assessed by verifying that lung volumes changed less than 0.1 mL/minute over 3 minutes at 30 cm $H_2O$ pressure. Treatment groups consisted of 12 preterm rabbits. All experiments were performed humanely and with the approval of the Animal Care and Use Committee of the Harbor-UCLA Medical Center Research and Education Institute.

Figure 9:
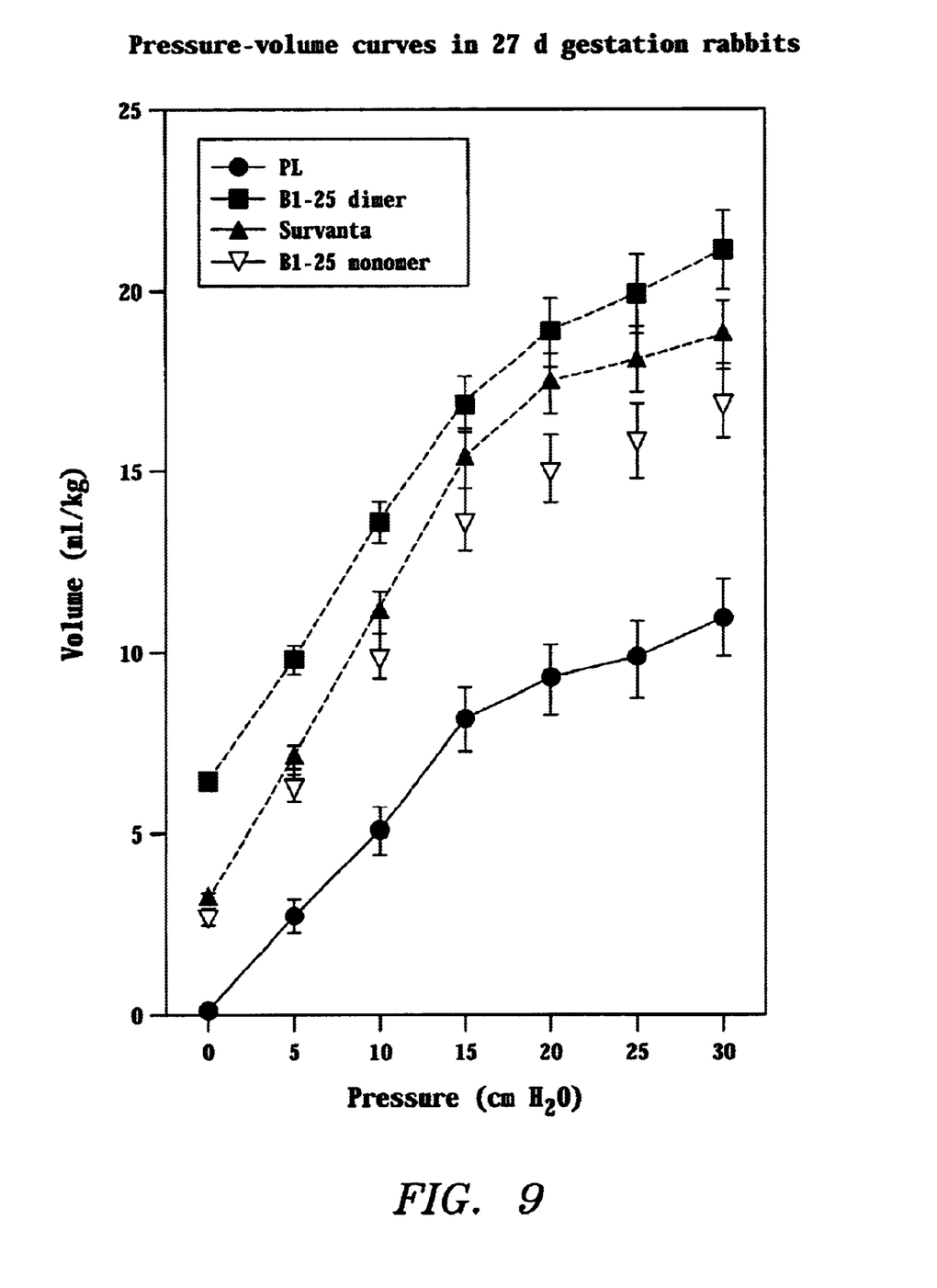
FIG. 9 is a measurement of preterm rabbit lung volume as a function of pressure comparing a standard phospholipid mixture (PL) -●-, Survanta -▲-, the SP-B1–25 monomer -▽-, and the SP-B1–25 dimer of the present invention -■-.

Postmortem pressure-volume curves showed that lung volumes at 30 cm $H_2O$ pressure were highest for preterm rabbits treated with B1–25 dimer surfactant, followed by Survanta® and B1–25 monomer surfactant, and lowest for PL-surfactant (FIG. 9). All values are expressed as means±standard error (SEM).

While the invention is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims. All references cited herein are specifically incorporated by reference in their entirety.

What is claimed is:

1. A peptide analog of lung surfactant protein B comprising:
   a dimer of a synthetic peptide consisting of amino acid residues 1–25 of SEQ ID NO: 2.

2. A peptide analog of lung surfactant protein B comprising:
   a dimer of a synthetic peptide consisting of amino acid residues 1–25 of SEQ ID NO: 3.

3. The peptide analog of claim 1 having a Cys 8 to Cys 8 disulfide link.

4. A pharmaceutical composition comprising:
   a peptide analog of lung surfactant protein B comprising a dimer of a synthetic peptide consisting of amino acid residues 1–25 of SEQ ID NO: 2; and
   an animal derived lung surfactant comprised of natural lung surfactant proteins.

5. A pharmaceutical composition comprising:
   a peptide analog of lung surfactant protein B comprising a dimer of a synthetic peptide consisting of amino acid residues 1–25 of SEQ ID NO: 3; and
   an animal derived lung surfactant comprised of natural lung surfactant proteins.

6. The pharmaceutical composition of claim 4, or 5 further comprising one or more phospholipids comprising at least 95% of the composition by weight percent.

7. A dimer peptide analog of mammalian lung surfactant protein B comprising monomer peptides consisting of SEQ ID NO: 2 having a Cys 8 to Cys8 disulfide link, wherein the monomer peptides contain an amphipathic α-helical domain.

8. The peptide analog of claim 1 wherein the dimer is a homodimer.

* * * * *

UNITED STATES PATENT AND TRADEMARK OFFICE
CERTIFICATE OF CORRECTION

PATENT NO. : 6,660,833 B1  Page 1 of 1
APPLICATION NO. : 09/515356
DATED : December 9, 2003
INVENTOR(S) : Frans J. Walther et al.

It is certified that error appears in the above-identified patent and that said Letters Patent is hereby corrected as shown below:

Column 1, lines 5 through 9, after the Title, please delete: "This invention was made in part from government support under Grant Nos. RO1 HL 55543 and RO1 HL 51177 from the National Institute of Health (NIH) of the United States. The U.S. Government may have certain rights in this invention."

and substitute therefore:

"This invention was made with Government support under Grant No. HL055543 awarded by the National Institutes of Health. The Government has certain rights in this invention."

Signed and Sealed this

Fourteenth Day of December, 2010

David J. Kappos
*Director of the United States Patent and Trademark Office*